United States Patent [19]

Mertens et al.

[11] Patent Number: 4,582,933

[45] Date of Patent: Apr. 15, 1986

[54] PROCESS FOR THE PRODUCTION OF N-(TERT-AMINOALKYL)ACRYLAMIDES

[75] Inventors: Richard Mertens, Krefeld; Kurt Dahmen, Monchen-Gladbach, both of Fed. Rep. of Germany

[73] Assignee: Chemische Fabrik Stockhausen GmbH, Krefeld, Fed. Rep. of Germany

[21] Appl. No.: 476,095

[22] Filed: Mar. 17, 1983

[30] Foreign Application Priority Data

Mar. 18, 1982 [DE] Fed. Rep. of Germany ....... 3209800

[51] Int. Cl.$^4$ ............................................ C07C 102/04
[52] U.S. Cl. .................................... 564/138; 564/141; 564/204
[58] Field of Search .................. 564/138, 141, 204

[56] References Cited

U.S. PATENT DOCUMENTS

| 2,595,907 | 5/1952 | Thomas et al. | 564/204 |
|---|---|---|---|
| 2,719,177 | 9/1955 | Coover et al. | 564/204 |
| 3,200,150 | 8/1965 | Pollard et al. | 564/141 |
| 3,652,671 | 3/1972 | Barron | 564/204 |
| 3,878,247 | 4/1975 | Moss et al. | 564/204 |
| 4,031,138 | 6/1977 | Nieh et al. | 564/204 |
| 4,228,102 | 10/1980 | Besecke et al. | 564/137 |

Primary Examiner—Charles F. Warren
Assistant Examiner—John A. Sopp
Attorney, Agent, or Firm—Sprung Horn Kramer & Woods

[57] ABSTRACT

This invention describes a process for the production of N-(tert-aminoalkyl)acrylamides by the reaction of acrylic acid with a suitable tertiary aminoalkylamine at a temperature of 150°–230° C. The aminoalkylamine and acrylic acid are reacted in equimolar quantities, preferably in the presence of an acidic or a basic catalyst.

8 Claims, No Drawings

PROCESS FOR THE PRODUCTION OF N-(TERT-AMINOALKYL)ACRYLAMIDES

This invention describes a process for the production of N-(tert-aminoalkyl)acrylamides which are particularly valuable in homo- and copolymerization process, resulting in the manufacture of homo- and copolymers which are useful as flocculating and dewatering aids for use in waste-water treatment and as aids in improving the dry and wet strength and also as retention aids.

A number of processes for the production of N-(tert-aminoalkyl)acrylamides may be found in the literature. For example, German DT-OS No. 25 02 247 teaches that during the conversion of acrylic acids or acrylic esters, respectively, with a double molar excess of N,N-dialkylalkylene diamines, the corresponding β-aminopropionic acid amides result and that the N-(tert-aminoalkyl)acrylamides can be produced from these by removal of the amino group from the β-position. However, the high pyrolysis temperatures required for this process promote the formation of undesirable by-products as well as polymerization of the acrylamides. Furthermore, the cleaning of the cracking products requires costly distillation technology. Accordingly, this two-stage operation has generally been considered unsatisfactory.

In the process described in German DT-OS No. 28 09 102 and DT-OS No. 28 16 516, the esters of the (meth)acrylic acid are converted to the N-substituted (meth)acrylamides with a sub-stoichiometric amount or only a slight excess of N,N-dialkylene diamine in the presence of dialkyl stannic oxide or iron ions, respectively. In this process, however, the desired (meth)acrylamides are not obtainable at satisfactory rates of yield. Furthermore, DT-OS No. 28 09 102 specifies that the operations must be carried out under pressure.

U.S. Pat. No. 3,652,671 describes a process for the production of N-(dialkylaminoalkyl)methacrylamides in which methacrylic acid and N,N-dialkylalkylene diamines in equimolar amounts are subjected to elevated temperatures. The Michael adduct is formed very rapidly from the salt—i.e. the N-(dialkylaminoalkyl)-2-methyl-β-alanine— and the latter is converted to N-(dialkylaminoalkyl)-methacrylamide at a temperature of from 140° to 230° C. However, this process has the disadvantage that only N-substituted methacrylamides can be produced from the corresponding methacrylic acid adducts and that acrylic acid amides cannot be produced by this route. The patent states that side reactions predominate when acrylic acid is used and that for the most part tar-like materials result. Only small quantities of the desired N-substituted acrylamides can be isolated.

Most surprisingly, it has now been found that N-(dialkylaminoalkyl)acrylamides of the general formula

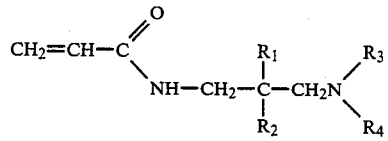

wherein $R_1$, $R_2$, $R_3$ and $R_4$ are in each instance straight or branched chain alkyl groups having 1–4 carbon atoms, can be produced in good yields by reaction of acrylic acid with tertiary aminoalkylamines of the formula

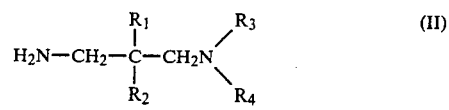

wherein $R_1$ to $R_4$ are as stated above at temperatures of from 120° to 300° C. (preferably 150°–230° C.). Preferably the water that results from this reaction is distilled off and preferably the acrylic acid and amine are in equimolar amounts.

The following tertiary aminoalkylamines of the general formula II are especially suitable for the invention:
3-dimethylamino-2,2-dimethylpropylamine
3-diethylamino-2,2-dimethylpropylamine
3-diethylamino-2,2-diethylpropylamine
3-dimethylamino-2,2-diethylpropylamine
Of these, 3-dimethylamino-2,2-dimethylpropylamine is preferred.

Completion of the reaction is very simple. The acrylic acid is added drop by drop to the N,N-dialkylalkylene diamine, which optionally contains a polymerisation inhibitor and, also optionally, a catalyst. When this is done, the temperature can rise above 100° C. Once addition has been terminated, the mixture is heated to a temperature of from 150° to 230° C., whereupon the theoretical quantity of water is distilled off over a period of 1 to 5 hours. The acrylamide that is formed is isolated by means of vacuum distillation. A good yield of N-(tert-aminoalkyl)acrylamides results, and these can be used for homo-and copolymerization without further processing.

Although it is not essential, it has been found advantageous to add catalytic quantities of alkaline or acidic substances in a quantity of approximately 0.5–2% wt., related to the total weight of the reactants. These can be either non-organic (such as hydrochloric acid, phosphoric acid, calcium carbonate, or potassium hydroxide) or organic (for example, acetic acid, sodium acetate, or alcoholates). In the same way, Lewis acids and bases or ion exchange agents can be used. Phosphoric acid and borium trifluoride are preferred.

The reactions can be carried out in the presence of conventional polymerization inhibitors—such as, for example, p-dioxybenzol, p-methoxyphenol, copper powder, or copper salts. Aromatic amines—such as, for example, N-phenyl-β-naphthylamine, N,N'-diphenyl-p-phylenediamine or phenothizine—are preferred.

The invention will now be described with reference to the foregoing examples, which are for purposes of illustration only:

EXAMPLE 1

A 500-ml three-neck flask fitted with a magnetic agitator, a thermometer, and a short column with a distillation set was charged with 260 g (2 mol) 3-dimethylamino-2,2-dimethylpropylamine; 4 g N-phenyl-β-naphthylamine; and 4 ml 85% phosphoric acid. 144 g (2 mol) acrylic acid was added drop by drop for 0.5 hours, whereupon the temperature of the mixture rose to 150° C. Finally, the mixture was heated to 200° C. in a nitrogen atmosphere for 2 hours, and then stirred at this temperature for 1 hour. During this time, 35.5 g of the distillate was obtained. Distillation was carried out in a vacuum after cooling and 247 g (67%) N-(3-dimethylamino-2,2-dimethylpropyl)acrylamide, boiling point 110°–115° C. at 66.5 Pa, was obtained.

EXAMPLE 2

Proceeding as in Example 1, 260 g 3-dimethylamino-2,2-dimethylpropylamine; 144 g acrylic acid; 4 g N,N′-diphenylenediamine; and 10 ml BF3-etherate were mixed. It was found possible to isolate 265 g (72%) of the N-(3-dimethylamino-2,2-dimethylpropyl)acrylamide.

EXAMPLE 3

Proceeding as in Example 1, 60 g 3-diethylamino-2,2-dimethylpropylamine; 27.3 g acrylic acid; 1.0 g N,N′-diphenyl-p-phenylenediamine; and 1 ml 85% phosphoric acid were mixed. 47.5 g (59%) N-(3-diethylamino-2,2-dimethylpropyl)acrylamide, boiling point 139° to 141° C. at 1.33 Pa, were isolated.

EXAMPLE 4

Proceeding as in Example 1, 173.5 g 3-dimethylamino-2-ethyl-2-butylpropylamine; 67 g acrylic acid; 2 g N,N′-diphenyl-p-phenylenediamine; and 2 g calcium tert-butylate were mixed. 122 g (55%) N-(3-dimethylamino-2-ethyl-2-butylpropyl)-acrylamide, boiling point 129° C. at 66.5 Pa, was isolated.

EXAMPLE 5

Proceeding as in Example 1, 130 g 3-dimethylamino-2,2-dimethylpropylamine; 72 g acrylic acid; 3 g copper acetate; and 2 g 85% phosphoric acid were mixed. 130.5 g (71%) N-(3-dimethylamino-2,2-dimethylpropyl)acrylamide was isolated.

The embodiments of the invention in which an exclusive property or privilege is claimed are defined as follows:

1. A process for preparing an N-(tert-aminoalkyl)acrylamide of the general formula

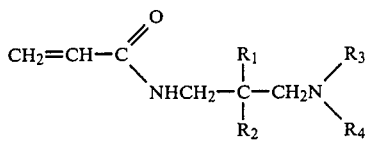

wherein $R_1$, $R_2$, $R_3$ and $R_4$ are in each instance a straight or branched chain $C_1$ to $C_4$-alkyl group, comprising reacting acrylic acid with an approximately equimolar amount of a tertiary aminoalkylamine of the general formula

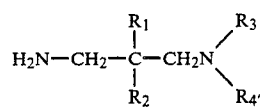

wherein $R_1$, $R_2$, $R_3$ and $R_4$ are as hereinbefore defined at about 120° C. to 300° C.

2. A process according to claim 1, wherein the reaction temperature is from about 150° C. to 230° C.

3. A process according to claim 1, wherein the reaction is performed in the presence of catalytic quantities of acidic or basic substances.

4. A process according to claim 3, wherein said acidic or basic substances are selected from organic and inorganic acids and bases, Lewis acids and bases, and ion-exchange agents.

5. A process according to claim 1, wherein the reaction is performed in the presence of one or more polymerization inhibitors selected from the group consisting of p-dioxybenzol, p-methoxyphenol, N-phenyl-β-naphthylamine, phenotiazine, N,N-diphenyl-p-phenylenediamine, copper powder and copper salts.

6. A process according to claim 1, wherein the N-(tert-aminoalkyl)acrylamide product is isolated from the reaction mixture by distillation.

7. A process according to claim 3, wherein the reaction is performed in the presence of one or more polymerization inhibitors selected from the group consisting of p-dioxybenzol, p-methoxyphenol, N-phenyl-β-naphthylamine, phenotiazine, N,N-diphenyl-p-phenylenediamine, copper power and copper salts.

8. A process according to claim 3, wherein the N-(tert-aminoalkyl)acrylamide product is isolated from the reaction mixture by distillation.

* * * * *

UNITED STATES PATENT AND TRADEMARK OFFICE
CERTIFICATE OF CORRECTION

PATENT NO.  : 4,582,933
DATED       : April 15, 1986
INVENTOR(S) : Richard Mertens, et al.

It is certified that error appears in the above-identified patent and that said Letters Patent is hereby corrected as shown below:

Col. 2, line 51    "phenothizine" should read -- phenothiazine --.

Col. 2, line 53    Delete "examples" and substitute --Examples--

Col. 3, line 9     Delete "diphenylenediamine" and substitute --diphenyl-p-phenylene-diamine--

Col. 4, line 45    Delete "power" and substitute --powder--

Signed and Sealed this

Fifth Day of August 1986

[SEAL]

Attest:

DONALD J. QUIGG

Attesting Officer    Commissioner of Patents and Trademarks